(12) United States Patent
Costin

(10) Patent No.: US 6,555,534 B1
(45) Date of Patent: *Apr. 29, 2003

(54) METHOD AND COMPOSITIONS FOR THE CONTROL OR ERADICATION OF *HELICOBACTER PYLORI*

(75) Inventor: James C. Costin, Lower Gwynedd, PA (US)

(73) Assignee: Medpointe Healthcare Inc., Somerset, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/266,095

(22) Filed: Mar. 10, 1999

Related U.S. Application Data

(63) Continuation-in-part of application No. 09/151,885, filed on Sep. 11, 1998.

(51) Int. Cl.[7] .................. A61K 31/54; A01N 63/00; C07D 285/16

(52) U.S. Cl. .................. 514/222.5; 514/925; 514/926; 514/927; 424/93.4; 544/8

(58) Field of Search .................. 424/93.4; 514/222.5, 514/925, 926, 927; 544/8

(56) References Cited

U.S. PATENT DOCUMENTS 5,476,854 A * 12/1995 Young .................. 514/254
6,011,030 A * 1/2000 Pfirrmann .................. 514/222.2

OTHER PUBLICATIONS

J. Ian Blenkharn, "Sustained anti–adherence activity of Taurolidine (Taurolin) and Noxythiolin (Noxyflex S) solutions", J. Pharm. Pharmaco., Jan. 4, 1988, 40:509–511.*

J. Ian Blenkharn, "In–vitro Antibacterial Activity of Noxythiolin and Taurolidine", J. Pharm. Pharmacol., Mar. 26, 1990, 42: 589–590.*

* cited by examiner

*Primary Examiner*—James O. Wilson
*Assistant Examiner*—Everett White
(74) *Attorney, Agent, or Firm*—Elliot M. Olstein; Raymond E. Stauffer

(57) ABSTRACT

The use of 4,4-methylenebis (tetrahydro-1,2-4-thiadiazine-1,1-dioxide) in the eradication and control of the microorganism *Helicobacter pylori* in humans is disclosed.

6 Claims, No Drawings

METHOD AND COMPOSITIONS FOR THE CONTROL OR ERADICATION OF *HELICOBACTER PYLORI*

This application is a continuation-in-part of U.S. application Ser. No. 09/151,885 filed Sep. 11, 1998.

This invention relates to a method and compositions for the treatment of bacterial infection which reduces or eliminates the presence of bacteria. Moreover, this invention relates to a method and compositions for the reduction or elimination of *Helicobacter pylori*.

Specifically, the present invention relates to the use of 4,4' methylenebis(tetrahydro-1,2,4-thiadiazine-1,2-dioxide) known generically as taurolidine to treat bacterial infections, particularly *Helicobacter pylori* infections.

Taurolidine occurs as a white to off-white powder having the molecular formula — $C_7H_{16}N_4O_4S_2$.

Taurolidine's general characteristics include acceptable stability in the solid state when stored at ambient conditions, melting with decomposition at approximately 170° C. and the following solubility in aqueous solutions and organic solvents.

| | |
|---|---|
| Water | 1% at 20° C. |
| Dilute HCl | soluble |
| Dilute NaOH | soluble |
| $CHCl_3$ | insoluble |
| EtOH | sparingly soluble |
| DMF | 1 g in 2 mL/ca.60° C. |
| Acetone | 1 g in 120 mL/Boiling |
| Ethanol | 1 g in 130 mL/Boiling |
| Methanol | 1 g in 170 mL/Boiling |
| Ethyl Acetate | 1 g in 200 mL/Boiling |

A saturated solution of taurolidine in deionized water has a pH of 7.4. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents including USA 3,423,408; Switzerland No. 482,713 and United Kingdom No. 1,124,285 and is carried out in five stages:

Potassium phthalimidoethane sulphonate is prepared from taurine, phthalic anhydride, glacial acetic acid and potassium acetate;

Potassium phthalimidoethane sulphonate is then converted to phthalimidoethane sulphonylchloride by chlorination with phosphorous oxychloride;

Phthalimidoethane sulphonylchloride is reacted with ammonia to form phthalimidoethane sulphonamide;

Phthalimidoethane sulphonylchloride is reacted with hydrazine hydrate and in the subsequent hydrazinolysis to form taurinamide hydrochloride; and Taurolidine is prepared from taurinamide hydrochloride and formaldehyde.

The antimicrobial actions of taurolidine have been described in U.S. patent application Ser. No. 09/151,885 filed Sept. 11, 1998 and in U.S. Pat. No. 3,423,408 and elsewhere in the literature. In addition, the following United States Patents describe various uses for and compositions containing taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine's mechanism of action unlike that of known antibiotics is based on a chemical reaction. While not being bound by any theory, during the metabolism of taurolidine to taurinamide and ultimately taurine and water, methylol groups are liberated which chemically react with the mureins in the bacterial cells walls this results in the denaturing of the complex polysacchardide and liposaccharide components of the bacterial cell wall as well as changing the double stranded DNA of the plasmid to a denatured or single stranded DNA.

Taurolidine has been shown to be safe and well tolerated at systemic doses exceeding 40 g/day and cumulative doses up to and exceeding 300 g.

The formulations of taurolidine generally utilized are sterile solutions containing 0.5%, 1.0% or 2.0% taurolidine for irrigation/lavage, wound instillation, or intravenous administration, primarily for the treatment or prevention of peritonitis, sepsis or osteitis/osteomyelitis. In addition, topical surgical gels containing 2.0% to about 4.0% are utilized for the treatment of osteitis/osteomyelitis.

It has long been the goal of the pharmaceutical industry to produce antibiotic medicinal substances that have the power to kill—or at least to arrest the growth of—many disease causing bacteria such as *Helicobacter pylori*.

Much has been published regarding *Helicobacter pylori* itself. Helicobacter pylori is approximately 0.85 $\mu$m in diameter with an average length of 2.9 $\mu$m. The microorganism has a smooth coat and four to six polar flagella which are sheathed and have bulbous ends. In fresh cultures this organism appears as a slender, curved Gram-negative rod. *Helicobacter pylori* is readily distinguished from other gastric bacteria and spirochaetes by the absence of axial filaments in its flagella. Furthermore, optimum growth conditions for *Helicobacter pylori* are unusual and help to set it apart from other enteropathogens. For example, *Helicobacter pylori* requires a microaerophilic gas environment (i.e. low oxygen content) to sustain growth. *Helicobacter pylori* appears tolerate a wide range of local pH conditions and is relatively resistant to acid conditions. It is believed that this resistance is due in part to the organism's outer protein structure which contains urease in large amounts resulting in the cleavage of urea naturally present in gastric fluid and hence, the formation of a buffering ammonia layer immediately around the organism.

Although a number of spiral bacteria inhabit the mouth and lower intestinal tract of all mammals, what distinguishes *Helicobacter pylori* is the observation that it is localized almost exclusively to the luminal mucosal surface of the stomach and duodenum and generally is found deep within the gastric pits.

It is the combination of the unusual growth requirements and intestinal location which makes eradication and treatment of *Helicobacter pylori* so difficult. The ideal antimicrobial drug suitable for the successful treatment of *Helicobacter pylori* associated gastritis should exhibit local activity, be stable at low pH values and should be able to readily penetrate the gastric mucosa. These desirable properties of an antimicrobial are not easily accomplished and thus, satisfactory treatment of *Helicobacter pylori* with antimicrobials has yet to be accomplished.

The development of an agent which is effective in the management of *Helicobacter pylori* induced gastritis would fulfill a long felt need. There is an emerging consensus in the field of gastroenterology that *Helicobacter pylori* is a major contributing factor in the development of gastritis and septic ulcer disease. Specifically, the following reference is useful in establishing the background of the present invention: *Campylocacter pylori*, E. A. J. Rauns and G. N. J. Tytgat, Editors, Adis Press Intntl. (1989).

The present invention relates to a method and composition for the eradication of the microorganism *Helicobacter pylori* (formerly referred to in the literature as *Campylobacter pylori*). In its broadest aspect, the present invention is directed to novel compositions which demonstrate antimicrobial activity against *Helicobacter pylori*.

Moreover, owing to its chemical mechanism of action with the bacterial cell wall, taurolidine is fully effective against *Helicobacter pylori* which are resistant to other antibiotics. Further, treatment of *Helicobacter pylori* with taurolidine reduces or eliminates the ability of the bacteria to acquire resistance to antibiotic drug treatment.

Peptic ulcers, once thought to result from stress, or excess acidity, or a reduction of the mucosal defense factors in the stomach, are now in a majority of cases considered to be the result of bacterial infection by *Helicobacter pylori*. The mounting evidence to this effect is well documented in *Helicobacter pylori* in Peptic Ulceration and Gastritis, edited by Barry J. Marshall, Richard W. McCallum and Richard L. Guerraut, Blackwell Scientific Publications, Boston, U.S.A. Pertinent Chapters in this work include Chapter four, The Epidemiology of *Helicobacter pylori* Infection by D. N. Taylor and M. J. Blaser; Chapter seven, Laboratory Diagnosis and Handling of *Helicobacter pylori*, by T. U. Westblom; and Chapter twelve, Practical Diagnosis of *Helicobacter pylori* by B. J. Marshall. The history of the discovery of *Helicobacter pylori* and its association with gastro intestinal disease is extensively described in "Marshall's Hunch, " The New Yorker magazine, pages 64–72, Sep. 20, 1993 and "The Doctor Who Wouldn't Accept No, " Reader's Digest magazine, pages 120–124, Oct. 1993.

The effect of treatment of *Helicobacter pylori* Infection on long term recurrence of Gastric or Duodenal Ulcer is described by David Y. Graham et al. In Annals of Internal Medicine 1992; 116: No. 9.

*Helicobacter pylori* has now been shown to be the causative agent for most instances of chronic gastritis. And, it is now known that, in the absence of aspirin, non-steroidal anti-inflammatory drugs or hypersecretory states, this bacteria is directly implicated in the production of peptic ulcer diseases such as duodenal and benign gastric ulcers. The eradication of *Helicobacter pylori* gastritis by antibiotics has been shown to cure peptic ulcers and prevent recurrence.

Presently, the main therapies employed in the treatment of chronic active gastritis and peptic ulcer disease include the histamine H2-receptor antagonists, bismuth compounds, and antibiotics. However, it is generally accepted that all currently used treatment modalities are clinically inadequate since post-treatment relapse rates remain unacceptably high. In addition, several of these therapies are accompanied by significant side effects. For example, effective antibiotic treatment of *Helicobacter pylori* infections requires treatment over an extended duration (4–6 weeks) and results in the induction of diarrhea and intestinal discomfort. The bismuth compounds are also known to have a number of significant undesirable side effects.

To date, the preferred treatment has been dominated by the use of H2-antagonists which result in the suppression of acid and pepsin secretion; however, post treatment relapse rates are extremely high. Since symptomatic relief and ulcer healing are the primary aim of treatment, without indefinite maintenance therapy, it is becoming increasingly apparent that a mucosal "protective agent " having antimicrobial activity against *Helicobacter pylori*, is desirable.

Thus, the medical community has a need for a protective agent which can be readily utilized in pharmaceutical and/or nutritional formulations. The present invention fulfills that need.

The method for the eradication or control of the microorganism *H. pylori* in accordance with the present invention comprises the step of administering to a human infected with a gastrointestinal disorder an effective amount of Taurolidine either alone or in combination with another antibacterial agent such as metronidazole, ciproflaxin, amoxicillin, amoxicillin-clavulanic acid, piperacillin, cefoxitin, imipenem and clindamycin.

Taurolidine can be administered prior to, during or after administration of the additional antibacterial agent. It has been found that by combining taurolidine with other antibacterial agents the tendency of the microorganisms to develop resistance to such antibacterial agents is reduced.

In general, the compositions of the present invention can be readily utilized in pharmaceutical and/or nutritional formulations, preferably formulations which release taurolin quickly in the stomach. The disclosed medicament may be used alone or in combination with a pharmacologically and/or nutritionally acceptable carrier and may be in capsule, tablet, powder or liquid form.

The formulations of taurolidine generally utilized are sterile solutions containing about 0.5%, 1.0%, 2.0% or about 4.0% taurolidine.

The compositions for the eradication of *Helicobacter pylori* may take any of a variety of forms as noted, however, in terms of ability to deliver the active material to the target site of action, i.e. the stomach and duodenum (upper small intestine where most ulcers occur) it is preferred to use tablet, capsule, solution or suspension formulations.

Solid carriers and diluents suitable for use include sugars such as lactose and sucrose, cellulose derivatives such as carboxymethyl cellulose, ethylcellulose, methylcellulose, etc., gelatin including hard and soft gelatin capsules, talc, cornstarch, stearic acid and magnesium stearate.

Suspension formulations may additionally contain benzoic acid, coloring, natural and artificial flavors, glycerin, kaolin, magnesium, aluminum silicate, methyl paraben, pectin, purified water, saccharin, sodium hydroxide and sucrose.

The percentage of taurolidine in the composition can be varied over wide limits and the quantity of medicament furnished by each individual tablet, capsule, solution or suspension is relatively unimportant since the indicated daily dose can be reached by administering either one or a plurality of capsules, tablets or suspensions.

The following non-limiting Examples are provided to illustrate further the present invention:

EXAMPLE 1

Solution

Taurolidine: 400 g

Polyvinylpyrrolidone: 100 g

Sterile Water to: 20 liters

15 Liters double distilled pyrogen free water are filled into a 25 liter glass vessel with stirrer and intensive reflux device and heated to 50° C. with stirring. The taurolidine 400 g is added followed by polyvinylpyrrolidone 1000 g. After dissolution, the solution is cooled and the pH adjusted to 6.0 with a few drops of 0.1 N hydrochloric acid. The solution is then passed through an adsorption filter to remove microorganisms and pyrogens and through a sterilising millipore filter before being filled into 100 ml vials which are finally autoclaved.

EXAMPLE 2

Solution

Taurolidine: 990 g

Sterile Water ad: 22 liters

The taurolidine is dissolved in the sterile water and filled into sterile bottles, 250 ml in each.

EXAMPLE 3

Tablet

Taurolidine: 500 g

Amylum maydis: 60 g

Kollidone 25: 50 g (polyvinylpyrrolidone)

Plasdon XL: 20 g

Magnesium stearate: 6 g

Distilled water: 200 g 1000 tablets, each containing 500 mg taurolidine, are produced by conventional means using the above formulation.

In an alternative tablet formulation, the amylum maydis is replaced by 60 g amylum orizae.

EXAMPLE 4

Solution

Taurolidine: 440 g

Pharmaceutical gelatin: 88 g

Sodium chloride: 99 g

Sterile water to: 22 liters

The components are dissolved in the sterile water, if necessary using gentle warming and sonication. The solution is then filled into sterile bottles, 500 ml in each.

The foregoing description is given for clearness of understanding of the invention only, and no unnecessary limitations should be understood therefrom, as modifications will be obvious to those skilled in the art.

I claim:

1. A method of treating a human infected with a gastrointestinal disorder induced by *Helicobacter pylori* comprising enterally administering to the individual in need of such treatment an effective amount of a composition comprising 4,4-methylenebis(tetrahydro-1,2,4-thiadiazine-1,1dioxide) in an amount effective to treat the bacterial infection caused by *Heliobacter pylori* present in the luminal mucosal surface of the stomach and duodenum.

2. A method according to claim wherein the gastrointestinal disorder is peptic ulcer disease.

3. A method according to claim 1 wherein the composition is in capsule form.

4. A method according to claim 1 wherein the composition is in tablet form.

5. A method according to claim 1 wherein the composition is in suspension form.

6. A method according to claim 1 wherein the composition is in solution form.

* * * * *

UNITED STATES PATENT AND TRADEMARK OFFICE
CERTIFICATE OF CORRECTION

PATENT NO.   : 6,555,534 B1
DATED        : April 29, 2003
INVENTOR(S)  : Costin

It is certified that error appears in the above-identified patent and that said Letters Patent is hereby corrected as shown below:

Column 1,
Line 13, delete "1,2-dioxide" and insert -- 1, 1-dioxide --.
Line 59, after "described in" and before "U.S. patent application Ser. No. 09/151,885" insert -- co-pending --.

Column 2,
Line 43, after "appears" and before "tolerate" insert -- to --.

Signed and Sealed this

Eighth Day of November, 2005

JON W. DUDAS
*Director of the United States Patent and Trademark Office*